United States Patent [19]

Teramoto et al.

[11] Patent Number: 5,200,400
[45] Date of Patent: Apr. 6, 1993

[54] METHOD FOR INHIBITING ALLOGRAFT REJECTION USING PHOTOACTIVATABLE NUCLEOTIDES OR NUCLEOSIDES

[75] Inventors: Kenichi Teramoto; Melvin E. Clouse, both of Brookline, Mass.

[73] Assignee: New England Deaconess Hospital Corporation, Boston, Mass.

[21] Appl. No.: 731,191

[22] Filed: Jul. 12, 1991

[51] Int. Cl.$^5$ ............................ A01N 43/04; A01N 43/54
[52] U.S. Cl. ............................................ 514/45; 514/46; 514/47; 514/49; 514/50; 514/51; 514/256; 514/274; 514/885
[58] Field of Search ................. 514/256, 885, 274, 45, 514/50, 49, 51, 46, 47

[56] References Cited

U.S. PATENT DOCUMENTS 4,894,364  1/1990  Greer ................................. 514/49
5,028,594  7/1991  Carson ............................... 514/23

OTHER PUBLICATIONS

Mishell et al *Selected Methods in Cellular Immunology*, pp. 238–239 1986.
Roitt et al *Immunology* p. 24.8 1985.
Goodman et al *The Pharmacological Basis of Therapeutics* pp. 1268–1276 1985.
Teramoto et al "DNA Synthesis . . . " Biosis Abst. #90096965 of *Transplantation* 50(2):199–201 1990.
B. Shutte et al., "Studies With Anti-bromodeoxyuridine Antibodies: II. Simultaneous Immunocytochemical Detection of Antigen Expression and DNA Synthesis by In Vivo Labeling of Mouse Intestinal Mucosa", 1986.
B. Schutte et al., "An Improved Method for the Immunocytochemical Detection of Bromodeoxyuridine Labeled Nuclei Using Flow Cytometry", vol. 8, 1987, pp. 372–376.
M. Pallavicini et al., "Cytokinetic Properties of Asynchronous and Cytosine Arabinoside Perturbed Murine Tumors Measured by Simultaneous Bromodeoxyuridine/DNA Analyses", Cytometry, vol. 6, 1985, pp. 602–610.
Kinsella, Timothy J., M.D. et al., "The Use of Halogenated Thymidine Analogs as Clinical Radiosensitizers: Rationale, Current Status, and Future Prospects: Non-Hypoxic Cell Sensitizers", Radiation Oncology, vol. 10, No. 8, Aug. 1984, pp. 1399–1406.
Kinsella, Timothy J. M.D. et al., "A Phase I Study of Intermittent Intravenous bromodeoxyuridine (BUdR) With Conventional Fractioned Irradiation", Radiation Oncology, vol. 10, No. 1, Jan. 1984, pp. 69–76.
T. Aoyama et al., "Effect of Halogenated Pyrimidines on Radiosensitivity of Mouse Strain L Cells and Their Radioresistant Variant", Journal of Radiation Research, vol. 5, No. 1, Mar., 1964, pp. 39–48.
F. Dolbeare et al., "Flow cytometric measurement of total DNA content and incorporated bromodeoxyuridine", Proc. Natl. Acad. Sci., vol. 80, Sep., 1983, pp. 5573–5577.
Kinsella, Timothy J. et al., "Continuous Intravenous Infusions of Bromodeoxyuridine As a Clinical Radiosensitizer", Journal of Clinical Oncology, vol. 2, No. 10, Oct. 1984, pp. 1144–1150.

(List continued on next page.)

[57] ABSTRACT

Method for inhibiting acute rejection of a transplanted organ or tissue by a recipient mammal that includes the steps of administering to the mammal a compound which causes selective sensitization of the alloreactive lymphocytes of the transplant recipient that are involved in the rejection process to a toxin; and exposing the mammal to the toxin to selectively destroy the sensitized alloreactive lymphocytes to a greater extent than non-sensitized cells of the mammal. This method induces donor specific tolerance in the transplant recipient, i.e., acceptance of the new organ or tissue without suppression of the rest of the recipient's normal immune system.

9 Claims, 3 Drawing Sheets

OTHER PUBLICATIONS

J. Kriss et al., "The Fate of 5-Bromodeoxyuridine, 5-Bromodeoxycytidine, and 5-Iododeoxycytidine in Man", Departments of Medicine and Radiology, Stanford University School of Medicine, pp. 260-261 1962.

Kinsella, Timothy J., M.D. et al., "A Phase I Study of Intravenous Idodeoxyuridine As a Clinical Radiosensitizer", Radiation Oncology, vol. 11, No. 11, Nov. 1985, pp. 1941-1946.

T. Ruers et al., "Cellular Proliferation At The Side Of Organ Allografts And The Influence Of Immunosuppresive Therapy", Transplantation, vol. 50, No. 4, Oct. 1990, pp. 568-572.

K. Sano et al., "A Therapy for Malignant Brain Tumors, Using Radiosensitizer (Bromouridine-Antometabolite-Continuous Intra-Arterial Infusion-Radiation Therapy)", University of Tokyo, p. 23 1972.

Kinsella, Timothy J., M.D., "Enhancement of X Ray Induced DNA Damage by Pre-Treatment With Halogenated Pyrimidine Analogs", I.J. Radiation Oncology, vol. 13, No. 5, May 1987, pp. 733-739.

*Primary Examiner*—Frederick E. Waddell
*Assistant Examiner*—Gregory Hook
*Attorney, Agent, or Firm*—Fish & Richardson

METHOD FOR INHIBITING ALLOGRAFT REJECTION USING PHOTOACTIVATABLE NUCLEOTIDES OR NUCLEOSIDES

BACKGROUND OF THE INVENTION

This invention relates to inhibition of acute rejection after organ transplantation.

Although transplantation of organs is becoming commonplace, rejection of the donated organ by the patient remains a serious problem. Except for cases of organ donation between identical twins or the special instance of transplantation in individuals with severe combined immunodeficiency disease, all transplant recipients currently require an immunosuppressive regimen to prevent rejection. Although these immunosuppressive drugs are administered in an attempt to prevent rejection, they also suppress the body's defenses against infection. Thus, transplantation requires a continued effort to induce acceptance of the graft without paralyzing the body's immune system.

Various regimens in use employ one or more of the following agents or therapies: (1) cortico-steroids, such as prednisone; (2) cytotoxic drugs, such as azathioprine and cyclophosphamide; (3) x-ray irradiation therapy; (4) anti-lymphocyte and anti-thymocyte globulins; (5) cyclosporine; and (6) monoclonal antibodies such as OKT3, which reacts specifically with the CD3 antigen-recognition structure of human T cells and blocks the T cell effector function involved in allograft rejection.

All of these therapy methods have undesirable side effects. For example, the corticosteroids may cause decreased resistance to infection, painful arthritis, osteoporosis, and cataracts. The cytotoxic agents may cause anemia and thrombocytopenia, and sometimes hepatitis. The antilymphocyte globulins may cause fever, hypotension, diarrhea, or sterile meningitis and are very expensive. Cyclosporine may cause decreased renal function, hypertension, tremor, anorexia, elevated low-density lipoprotein levels. OKT3 may cause chills and fever, nausea, vomiting, diarrhea, rash, headache, photophobia, and occasional episodes of life-threatening acute pulmonary edema.

X-ray irradiation therapy is currently used in leukemia patients undergoing bone marrow transplantation to produce marrow aplasia. The method is also used for renal and cardiac transplant patients who have responded inadequately to pharmacologic immunosuppression. Local irradiation to the grafted kidney has also been used to treat rejection.

There are two types of allograft rejection, acute humoral rejection (hyperacute rejection) and acute cellular rejection (acute rejection). Hyperacute rejection is generally an overwhelming, irreversible process that occurs when organs are transplanted into recipients who have preformed cytotoxic antibodies against antigens of the donor allograft. No combination of immunosuppressive drugs is capable of reversing this rapid process.

In contrast, acute rejection responds to treatment with immunosuppressive agents. Clinical manifestations of acute rejection may include fever, graft swelling or tenderness, oliguria, and increases in BUN and serum creatinine levels.

SUMMARY OF THE INVENTION

The present invention provides a method for inhibiting acute rejection of a transplanted organ or tissue by a recipient mammal that includes the steps of administering to the mammal a compound which causes selective sensitization of the alloreactive lymphocytes of the transplant recipient that are involved in the rejection process to a toxin; and then exposing the mammal to the toxin to selectively destroy the sensitized alloreactive lymphocytes to a greater extent than non-sensitized cells of the mammal. This method induces donor specific tolerance in the transplant recipient, i.e., acceptance of the new organ or tissue without suppression of the remainder of the recipient's normal immune system.

The sensitizing compound of the inventive method may be a DNA halogenator such as a halogen-containing nucleoside analog. In a preferred embodiment, this DNA halogenator is bromodeoxyuridine and the preferred toxin is irradiation of ultraviolet light.

The method may further include administering an antimetabolite to the mammal before exposing the mammal to the toxin. Examples are methotrexate, 5-fluorouracil, and fluorodeoxyuridine. By "antimetabolite" it is meant any compound that stimulates incorporation of the sensitizing compound by the lymphocytes. For example, it is known that 5-FU inhibits the biosynthesis of thymidine which results in forced incorporation of BUdR, a sensitizing compound, into newly synthesized DNA. Sato, K. et al. Neurol. Med. Chir. (Tokyo) 7:51–62 (1965).

Other features and advantages of the invention will be apparent from the following description of the preferred embodiments thereof, and from the claims.

DETAILED DESCRIPTION

The drawings are first briefly described. Drawings

USE OF BUdR AND INTERRADIATION TO INHIBIT REJECTION

The method of treatment of the invention selectively sensitizes the DNA of the alloreactive lymphocytes that begin to proliferate rapidly after a transplant. These alloreactive lymphocytes incorporate nucleoside analogs at a much higher rate than other cells, and thus can be selectively sensitized. More specifically, these cells, as they proliferate, incorporate nucleoside analogs that sensitize the DNA into the newly synthesized DNA, and consequently the entire cell, to toxins that kill the sensitized cells at dosages which are relatively safe for non-sensitized cells.

As an example of such sensitization, halogenation of DNA strands renders them more susceptible to irradiation, e.g., x-ray and UV light irradiation, which results in an increased sensitivity of their cells to irradiation. Therefore, any halogen-containing deoxynucleoside analogs, such as bromodeoxyuridine (BUdR), iododeoxy-uridine (IUdR), cholorodeoxyuridine (CUdR) or fluorodeoxyuridine (FUdR), would be suitable for the sensitization step of the invention.

Figure 1:
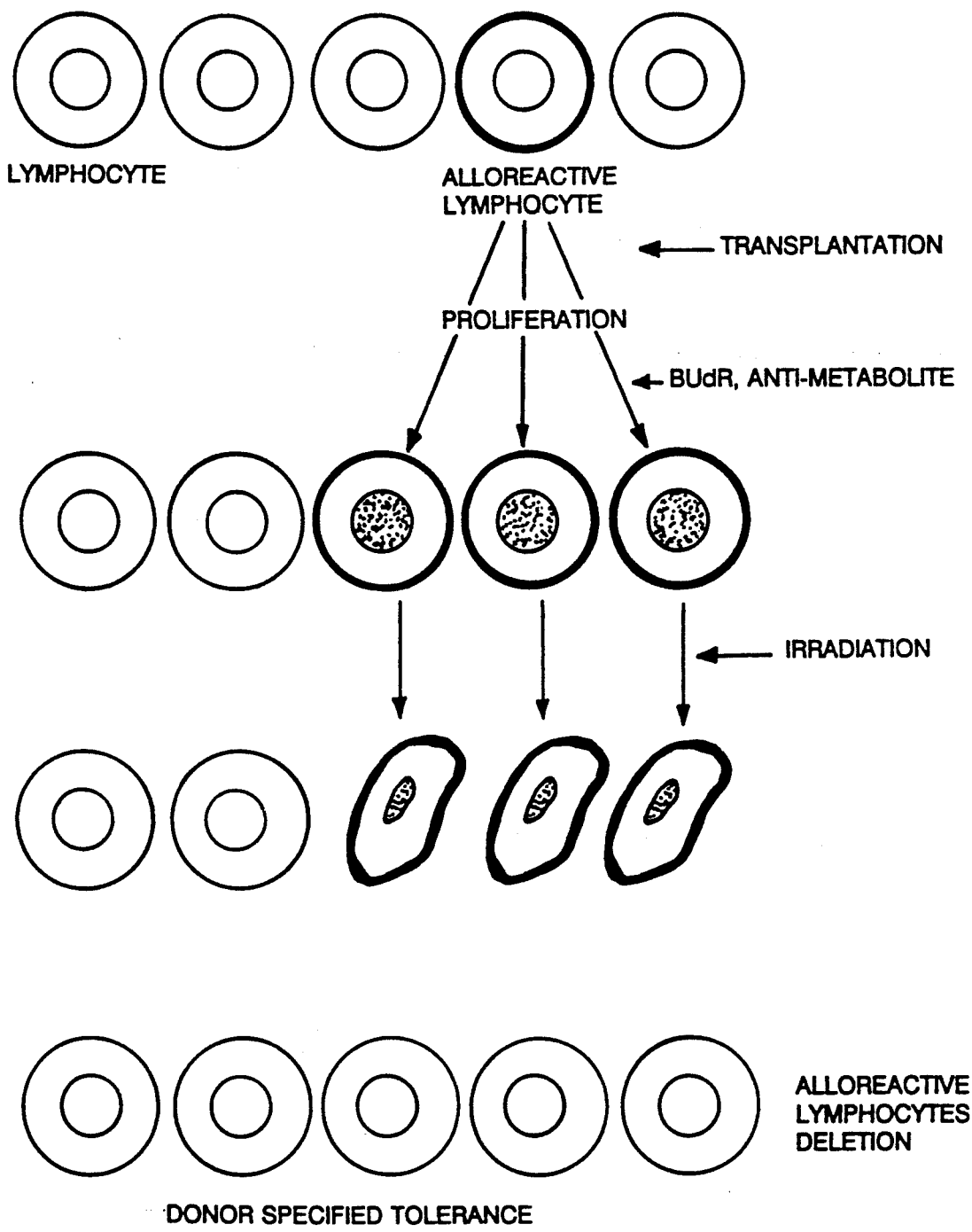
FIG. 1 is a scheme showing the steps of a treatment method of the invention.

In one embodiment, BUdR is administered to a transplant recipient so that it is inserted into the DNA of proliferating alloreactive lymphocytes. This increases the sensitivity of the DNA to irradiation, such as X-ray irradiation. The second step is to expose the transplant recipient to irradiation, either specifically in the region of the transplant or over the entire body, in a dosage that will destroy the sensitized lymphocytes, but will not significantly harm other, non-sensitized, cells. FIG. 1 schematically shows the steps of the invention leading to donor specific tolerance.

The uptake of BUdR into nuclei of dividing cells may be enhanced by the addition of a small amount of an enhancing agent, such as an antimetabolite, e.g., methotrexate, or 5-fluorouracil (5-FU). Such antimetabolites also serve the function of further removing harmful activated T-lymphocytes.

Other compounds useful to sensitize the alloreactive lymphocytes to irradiation include, but are not limited to, other dexoxynucleoside analogs cited above (i.e, IUdR, CUdR and FUdR). Furthermore, compounds that cause increased sensitivity of these lymphocytes to other toxins may be successful utilized for the method of the invention. In addition, compounds that cause increased toxin sensitivity of other, non-DNA cell components are also useful for the present invention.

The method according to the present invention includes an initial waiting period between transplantation of the allograft and administration of the sensitizing compound, to allow alloreactive lymphocyte proliferation to begin. This waiting period typically will be between 2 and 6 days, preferably 4 days. When using the sensitizing compound BUdR, the second step, exposing the recipient to irradiation, must occur soon (preferably within one day) after the injection of BUdR, because this compound is rapidly metabolized and eliminated from the DNA.

General transplantation techniques for the kidney, the heart, skin, and other organs and tissues are well known by those skilled in the art. In the examples given below, heterotopic heart transplants were performed on rats.

In human patients, the optimal dosages of BUdR and 5-FU, respectively would be 350–850 mg/m$^2$/12 hr, and irradiation would be 4,000–5,000 rad at 180 to 200 rad fractions over 4–5 weeks.

Application of the Method in the Rat Model

Experiments were done in which the hearts of male ACI donor rats (150–200 g) were transplanted to the right necks of Lewis recipient rats (200–250 g). See below "Heterotopic Heart Transplantation in Rat" for details. The recipient rats were then treated by intravenous injection of 10–100 mg/kg BUdR and/or 2.5–50 mg/kg of 5-FU on different postoperative days ("POD"). One hour after each BUdR and 5-FU injection, the rats were treated with 150–400 rad of irradiation.

Irradiation was done using GAMMACELL 40, Caesium 137 Irradiation Unit, Atomic Energy of Canada Limited, Ottawa, Canada. This unit has a caesium 137 double encapsulated source housed in each of two cylindrical sliding drawers one above and one below the sample cavity. The rat was laid in supine position in the sample cavity under anesthesia. With this machine, 1.8 minutes irradiation is necessary for 200 rad irradiation.

Three types of irradiation were performed. "Whole body" irradiation was performed from both above and below without using any lead plate to shield the rat. "Head, neck" irradiation was conducted from both above and below, using 8 mm thick lead plates to shield the body and limbs. In "graft" irradiation, only the heart graft was irradiated from above; 8 mm thick lead plates were used to shield other parts of the body.

In these experiments, five variables, i.e., timing of the treatment, irradiation doses, BUdR doses, 5-FU doses, site of irradiation, were investigated. In order to determine optimal timing and doses, thirteen groups of rats were used to perform various experiments. The results are shown in Table 1.

All four rats in Group 1 were not subjected to any treatment after the graft and survived for only 6, 7, 7 or 8 days, respectively, after graft. Rats in Group 2 were treated with BUdR and 5-FU or with 5-FU only, without irradiation. The results show that treatment with 10 mg/kg of BUdR and 5 or 25 mg/kg of 5-FU without irradiation was not effective. If the dose of 5-FU was increased to 50 mg/kg, the treatment without irradiation was effective. However, the recipients died before the heart graft stopped because of the toxicity of 5-FU. There was no difference in efficacy between the treatment timing of 4,5,6 POD and 2,4,6 POD.

"Whole body" irradiation was performed on rats in Group 3. Without treatment with BUdR and 5-FU, the irradiation was not very effective in inhibiting allograft rejection. With 50 mg/kg BUdR and 5 mg/kg 5-FU treatment, it effectively inhibited rejection. Although two rats died on days 12 and 14, respectively, after the transplantation, the heat grafts were in very good conditions.

TABLE 1

| | Treatment Days (POD) | BrdU (mg/kg) | 5-FU (mg/kg) | Site of Irradiation | rad | Days of Survival |
|---|---|---|---|---|---|---|
| 1. | — | No | No | | No | 6, 7, 7, 8 |
| 2. | 4, 5, 6 | 10 | 50 | | No | 15*, 15, 14 |
| | 2, 4, 6 | 10 | 50 | | No | 12*, 12*, 13* |
| | 4, 5, 6 | 10 | 5 | | No | 6, 7, 7 |
| | 4, 5, 6 | No | 50 | | No | 13, 13 |
| | 2, 4, 6 | No | 50 | | No | 12*, 15*, 16* |
| | 4, 5, 6 | 10 | 25 | | No | 11, 11 |
| | 2, 4, 6 | 10 | 25 | | No | 10, 10, 10 |
| 3. | 4, 5, 6 | No | No | Whole body | 150 | 8, 9, 10, 11 |
| | 4, 5, 6 | 50 | 5 | Whole body | 150 | 12*, 13, 14*, 14, 16 |
| 4. | 4, 5, 6 | 50 | 5 | Head, neck | 150 | 9, 11, 11, 13 |
| | 4, 5, 6, 7, 8 | 50 | 5 | Head, neck | 150 | 14, 18 |
| 5. | 4, 5, 6 | 50 | 5 | Head, neck | 300 | 11, 11, 12, 13 |
| | 3, 4, 5 | 50 | 5 | Head, neck | 300 | 12 |
| 6. | 3, 4, 5 | No | No | Graft | 150 | 5, 6, 6 |
| 7. | 3, 4, 5 | 50 | 5 | Graft | 150 | 7 |
| | 3, 4, 5, 6, 7 | 50 | 5 | Graft | 150 | 5, 7 |
| | 3, 4, 5, 8, 10, 12 | 50 | 5 | Graft | 150 | 18 |

TABLE 1-continued

| | Treatment Days (POD) | BrdU (mg/kg) | 5-FU (mg/kg) | Site of Irradiation | rad | Days of Survival |
|---|---|---|---|---|---|---|
| 8. | 3, 4, 5, 6, 7 | No | No | Graft | 400 | 7, 12 |
| 9. | 4, 5, 6, 7, 8 | 50 | 5 | Graft | 400 | 15*, 16* |
| | 3, 4, 5, 6, 7 | 50 | 5 | Graft | 400 | 12, 15* |
| | 2, 3, 4, 5, 6 | 50 | 5 | Graft | 400 | 14* |
| | 2, 4, 6, 8, 10 | 50 | 5 | Graft | 400 | 12, 18* |
| | 3, 4, 5, 8, 9 | 50 | 5 | Graft | 400 | 15*, 15* |
| 10. | 4, 5, 6, 7, 8 | 100 | 2.5 | Graft | 200 | 12, 14 |
| 11. | 4, 5, 6, 7, 8 | 100 | 2.5 | Graft | 250 | 10, 13 |
| 12. | 1–7, 10–13, 16–17 | 100 | No | No | No | ≧19 |
| 13. | 2–7, 11–13, 16–17 | 100 | No | Graft | 200 | ≧19 |

*Animals died but the condition of the heart graft was very good.

"Head, neck" irradiation was performed on rats in Groups 4 and 5. 3 day-treatment was to as effective as 4 day-treatment was successful; the latter resulted in survival for as long as 18 days.

Results from Group 6 show that 150 rad-irradiation on the graft only without treatment with BUdR and 5-FU was not effective. Further, as shown in results from Group 7, 150 rad-irradiation on the graft only, with 50 mg/kg BUdR and 5 mg/kg 5-FU treatment, for 3 or 4 days was not effective either; however, 6-day treatment resulted in survival for 18 days.

400 rad-irradiation for five days on the graft only, without administration of BUdR and 5-FU, was not very effective (Group 8). 400 rad graft irradiation, coupled with 50 mg/kgh BUdR and 5 mg/kg 5-FU treatment, for five days was effective; the graft of the rat that died on day 18 after the transplantation remained in good conditions (Group 9). Results from Groups 10 and 11 show that 200 or 250 rad irradiation started on day 4 was not as effective.

The result from Group 121 shows that if the treatment was begun on POD 1, even with only 100 mg/kg of BUdR and without irradiation and 5-FU, the rat survived for at least 19 days. This indicates that BUdR is an effective immunosuppressant by itself if given at a sufficiently high dosage without delay after transplantation. A similar result was obtained from an experiment with Group 13 in which the rat was graft-irradiated at 200 rad without treatment with 5-FU.

Mixed Lymphocytes Reaction

Mixed lymphocyte reaction ("MLR") is a method employed to monitor alloreactivity of lymphocytes. Briefly, lymphocytes from a stimulator animal is first treated with mitomycin-C or irradiation so that they cannot proliferate. The treated stimulator lymphocytes are then mixed with lymphocytes from a responder animal. The responder lymphocytes will start proliferating if they recognize antigen or antigens on the stimulator lymphocytes. Proliferation of the responder lymphocytes can be conveniently quantified by incorporation of radioactively labeled nucleosides as a result of DNA synthesis.

We carried out the MLR as follows. Lymphocytes were prepared from peripheral blood after Ficoll-Hypaque centrifugation. $2 \times 10^4$ responder lymphocytes were incubated with $2 \times 10^4$ irradiated stimulator lymphocytes in 20 $\mu$l volumes. The culture medium consisted of RPMI 1640 (Flow Lab, Costa Mesa, CA), containing 400 U/ml penicillin, 0.4 mg/ml Streptomycin, 1% of sodium pyruvate, 1% of L-glutamine-200 mM and 10% FCS (Gibco, Tulare, CA). After 96 hour-culture at 37° C. in a humidified atmosphere of 5% $CO_2$/95% air, the culture was pulsed with 0.2 $\mu$Ci $^3$H-methylthymidine ([$^3$H]TdR, specific activity 6.7 Ci/n-mol, Dupont, Boston, MA) and incubated for another 24 hours. The cells were then harvested onto glass fiber filter paper strips and radioactivity counted in a liquid scintillation counter (Beckman, Fullton, CA).

Figure 2:
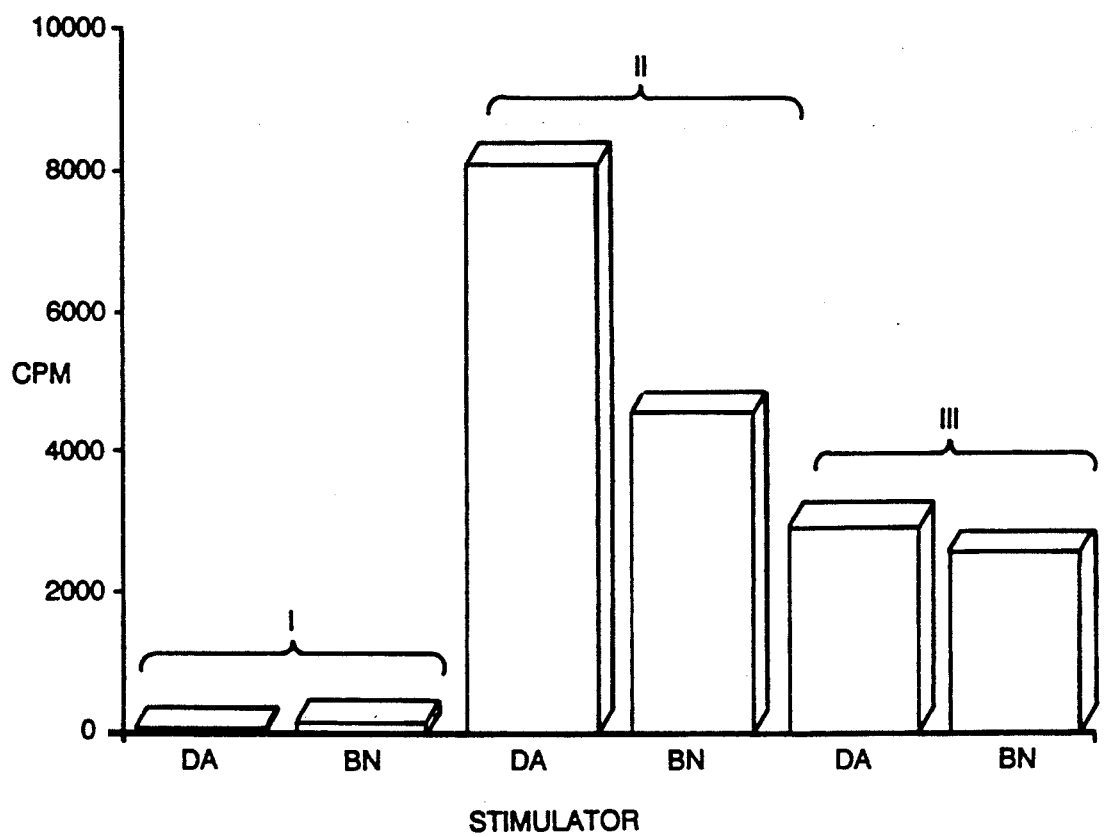
FIG. 2 is a graph of mixed lymphocytes reaction results of treated and untreated rats that received heart transplants.

Three MLR experiments were performed using lymphocytes from Lewis rats into which the heart from a DA rat had been transplanted as responder and lymphocytes from normal DA or BN rats as stimulator. The Lewis rats were either subjected to the treatment with 50 mg/kg, 5 mg/kg 5-FU and 150 rad irradiation on day 4 (Experiment I, FIG. 2, the two columns to the left), or were not treated at all (Experiment II, FIG. 2, the two columns in the middle). The results show that the lymphocytes from the DA heart-transplanted Lewis rats with treatment did not stimulate proliferation of the DA and BN lymphocytes, indicating the treatment induced unresponsiveness. By contrast, the lymphocytes from the DA heart-transplanted Lewis rats without treatment had high reactivity against the DA and BN lymphocytes. Experiment III was a control showing that the lymphocytes from normal Lewis rats stimulated proliferation of the DA and BN lymphocytes (FIG. 2, the two columns to the right).

Histological Observations

Figure 3:
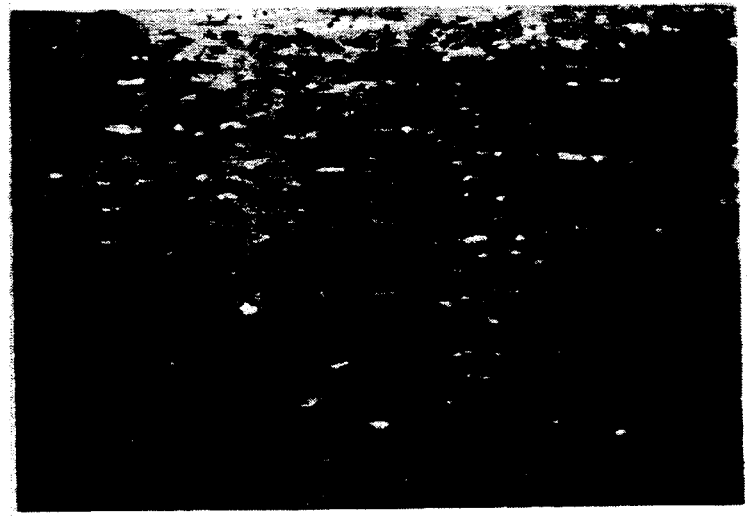
FIG. 3 is a photomicrograph of a section of a donor rat heart transplanted into a recipient rat treated according to the invention.

FIG. 3 is a photomicrograph of a section of a donor heart from a DA rat that was transplanted into a Lewis rat and treated (BUdR 50 mg/kg, 5-FU 5 mg/kg, 150 rad irradiation) on days 4, 5, 6. This sample was taken on day 9. This section of the transplanted heart from the treated rat reveals essentially normal histology. The myocytes are well preserved without evidence of necrosis. Perivascular and interstitial lymphocytes are rare.

Figure 4:
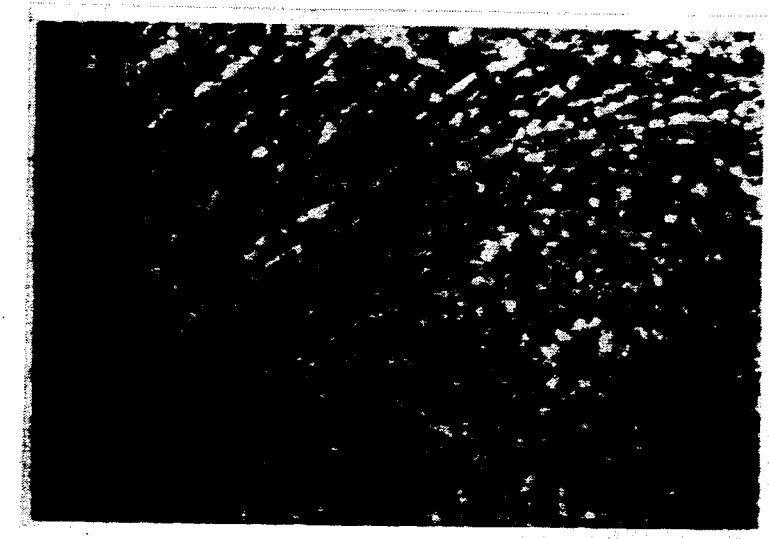
FIG. 4 is a photomicrograph of a section of a donor rat heart transplanted into an untreated recipient rat (control).

FIG. 4 shows a control sample that was taken on day 9 from a DA rat heart transplanted into a Lewis rat that was left untreated. This section of the transplanted heart from the untreated rat reveals evidence of acute rejection. There is a mild interstitial lymphocytic infiltrate, and myocyte necrosis is evident, both as individual fibers and in small irregular foci.

Preoperative Care

Rats were given free access to water and food. Anesthesia was induced by Metofane was confirmed by lack of a reaction to toe pinch, complete loss of consciousness, complete muscle relaxation, and stable respiration. To prepare for incision, the rat abdominal wall is shaved and sterilized with alcohol just before surgery.

Heterotopic Heart Transplantation in Rat

The donor rat was anesthetized deeply and the chest of the donor was opened. The donor was heparinized by IV injection of 0.2 ml of heparin. The pulmonary artery and aorta were divided following ligation of all other vessels. The heart was washed out with 3 ml of cold saline.

The recipient rat was also anesthetized deeply. An incision was made in the right neck of the recipient. The jugular vein and carotid artery were cross clamped and divided and cuffs were attached to them. The cuffed jugular vein was inserted into the lumen of the pulmonary artery of the graft. The carotid artery and the aorta of the graft were anastomosed in the same fashion. The incision was closed with 4–0 dexon.

Orthotopic Rat Liver Transplantation

Orthotopic liver transplants and skin grafts in rats may be performed as were the heterotopic heart transplants, in a number of experimental groups. Each group would have 3 to 5 recipients.

The donor rat is anesthetized deeply. A transverse abdominal incision is made. The attachments to the liver are first divided, and the right renal vein is ligated and divided from the vena cava. A fine piece of polyethylene tube is inserted into the donor bile duct. 0.2 ml of heparin is administered intravenously. The portal vein is divided from pyloric and splenic veins and cannulated with an 18G catheter and perfused with cold Ringer's solution. After removing the liver, cuffs for vascular connections are attached to the portal vein and the infrahepatic vena cava.

Under Metofane anesthesia, a midline incision is made in the recipient rat. The attachments to the liver are divided. The bile duct is cannulated by insertion of a 0.4 cm piece of 4FG tubing. The hepatic artery is ligated and cut, the IVC and portal vein are cross clamped with microvessel clips and the suprahepatic vena cava is cross clamped with a Satinsky clamp. The recipient liver is removed. The donor liver is placed in the orthotopic position and the suprahepatic vena cavae are anastomosed end-to-end with a 7–0 suture. The cuffed donor portal vein and IVC are inserted into the lumen of the recipient portal vein and IVC, respectively. The bile duct anastomosis is performed by telescoping the tube secured in the donor bile duct into the larger diameter tube secured in the recipient bile duct. The abdomen is then flushed with warm saline and closed in two layers with 3–0 silk. Following surgery, individually caged animals are kept warm under flood lights and receive daily injections of penicillin for one week.

Skin graft

The donor rat is anesthetized deeply. Full thickness skin (1.5 cm×1.5 cm) is taken from the donor rat's abdominal wall. The wound is closed with a continuous 4–0 dexon.

The recipient rat is anesthetized deeply. A piece of skin the same size as that removed from the donor is removed from the recipient rat's abdominal wall. The donor skin graft is put on the recipient's wound and sutured with a 4–0 dexon. A sterile dressing is applied and removed 7 days after the operation.

Other Embodiments

The foregoing description has been limited to specific embodiments of this invention. It will be apparent, however, that variations and modifications may be made to the invention, with the attainment of some or all of the advantages of the invention.

For example, while BUdR, a halogen-containing deoxynucleoside, was used in the working examples to sensitizing the alloreactive lymphocytes, other suitable compounds such as deoxynecleotide analogs, may also be used to achieve the desired effect. Other embodiments are also within the following claims.

What is claimed is:

1. A method for inhibiting rejection of a transplanted organ or tissue by a recipient mammal, said method comprising
   (a) after transplantation, introducing into the bloods stream of said mammal an effective amount of a pharmaceutical composition containing a photoactivatable nucleotide or nucleoside analog which causes selective sensitization of dividing alloreactive lymphocytes of said mammal; and
   (b) exposing said mammal to one effective dose of irradiation to destroy said sensitized dividing alloreactive lymphocytes to a greater extent than non-sensitized cells of said mammal.

2. The method of claim 1, wherein said photoactivatable nucleotide or nucleoside analog is a DNA halogenator.

3. The method of claim 2, wherein said DNA halogenator is a halogen-containing nucleoside analog.

4. The method of claim 3, wherein said nucleoside analog is bromodeoxyuridine.

5. The method of claim 2, wherein said irradiation is ultraviolet light irradiation.

6. The method of claim 1, wherein said pharmaceutical composition is introduced into the bloodstream intravenously.

7. The method of claim 2, wherein said pharmaceutical composition is introduced into the bloodstream intravenously.

8. The method of claim 1, wherein said irradiation is limited to the area in which said transplanted organ or tissue is located.

9. The method of claim 2, wherein said irradiation is limited to the area in which said transplanted organ or tissue is located.

* * * * *

UNITED STATES PATENT AND TRADEMARK OFFICE
CERTIFICATE OF CORRECTION

PATENT NO.   : 5,200,400

DATED        : April 6, 1993

INVENTOR(S)  : Kenichi Teramoto and Melvin E. Clouse

It is certified that error appears in the above-identified patent and that said Letters Patent is hereby corrected as shown below:

On the title page, item (56):
    Under "OTHER PUBLICATIONS" on page 2, column 1, "T. Ruers et al., 'Cellular Proliferation...', correct "Side" to --Site--;

Column 2, line 46, in the heading, correct "INTERRADIATION" to --IRRADIATION--;

Column 5, line 15, correct "was to as effective" to --was not as effective--;

Column 5, line 34, correct "Group 121" to --Group 12--.

Signed and Sealed this

Twenty-first Day of December, 1993

Attest:

BRUCE LEHMAN

*Attesting Officer*    *Commissioner of Patents and Trademarks*